United States Patent [19]
Drews

[11] Patent Number: 4,955,858
[45] Date of Patent: Sep. 11, 1990

[54] URETER DRAIN CATHETER RELEASABLY CLAMPED TO AN ADVANCING TUBE

[75] Inventor: Kurt Drews, Oststeinbek, Fed. Rep. of Germany

[73] Assignee: Uromed Kurt Drews GmbH, Oststeinbek, Fed. Rep. of Germany

[21] Appl. No.: 406,231

[22] Filed: Sep. 12, 1989

[30] Foreign Application Priority Data

Nov. 2, 1988 [DE] Fed. Rep. of Germany ....... 3837196

[51] Int. Cl.$^5$ .......................................... A61M 25/01
[52] U.S. Cl. ...................................... 604/8; 604/283; 128/657
[58] Field of Search ...................... 604/8–10, 604/283, 280, 264, 164, 165, 95, 93; 128/656–658

[56] References Cited

U.S. PATENT DOCUMENTS 4,547,194 10/1985 Moorehead .......................... 604/283
4,787,884 11/1988 Goldberg ................................ 604/8
4,875,489 10/1989 Messner et al. ...................... 604/283

FOREIGN PATENT DOCUMENTS 3339179 11/1985 Fed. Rep. of Germany .
G8614013.2 3/1986 Fed. Rep. of Germany .
3714839 5/1988 Fed. Rep. of Germany .

*Primary Examiner*—Stephen C. Pellegrino
*Attorney, Agent, or Firm*—Walter C. Farley

[57] ABSTRACT

A ureter drain catheter is detachably connected to an extension advancing tube by insertion of a cross sectionally reduced neck at the end of the advancing tube into the proximal end of the ureter drain catheter and is clamped by a mandrin extending through the advancing tube and into the neck in the drain catheter. The design of the neck is such that, at the clamping site, the mandrin is held in place on all sides by the snadwiched neck without making contact with the inner surface of the drain catheter.

3 Claims, 1 Drawing Sheet

U.S. Patent  Sep. 11, 1990  4,955,858
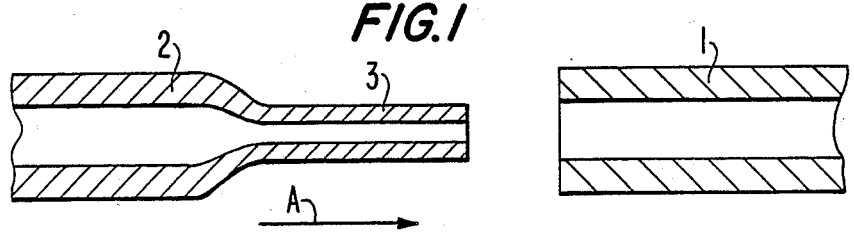
FIG.1
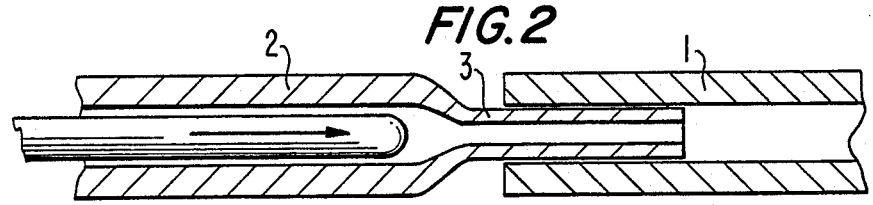
FIG.2
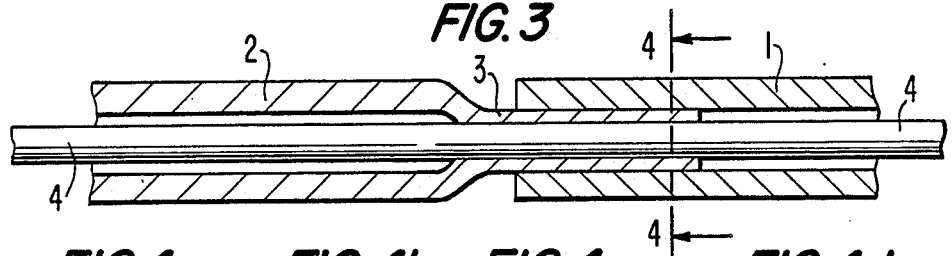
FIG.3
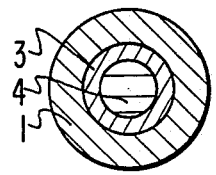 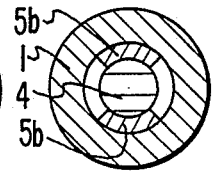 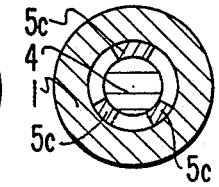 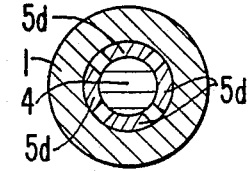
FIG.4a  FIG.4b  FIG.4c  FIG.4d
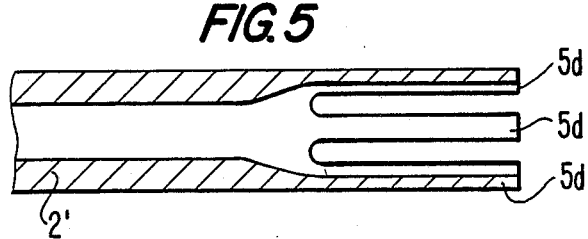
FIG.5

URETER DRAIN CATHETER RELEASABLY CLAMPED TO AN ADVANCING TUBE

This invention relates to a ureter drain catheter or tube of the kind used as a drain passage between the kidney and bladder and to an improved connection to an advancing tube and mandrin.

BACKGROUND OF THE INVENTION

Ureter drain tubes are used when a disease of the ureter connecting the kidney to the bladder hampers urine passage The drain tube assures urine elimination from the kidney. By means of an endoscope inserted through the urethra into the bladder, such a drain tube is advanced from the bladder through the ureter as far as the kidney and, as a rule, is designed in such a way that its ends lie respectively in the kidney and in the bladder and are held in place by their ends which are curved to prevent shifting. Apertures are provided at both ends to assure urine passage. Ureter drain tubes take the form of soft tubes a few millimeters in diameter.

To be insertable, these soft tubes are stiffened by an inserted, less flexible mandrin (wire or spiral-wire tube or combination of both) until reliable advancing without danger of kinking is possible, even through constrictions in the ureter.

Problems arise when multiple advancing and retraction is required at a ureter constriction in order to seek a suitable passageway.

Because the drain catheter length essentially is only enough for the distance from kidney to bladder, that is, the length is insufficient to pass through the inserting endoscope as far as the outside, an advancing tube always must be employed to allow advancing the drain tube. This advancing tube also is seated on the mandrin. The cited problems arise when retraction is desired outside of the endoscope. Neither retraction of the advancing tube nor retraction of the mandrin can be relied upon to pull back the possibly jammed drain tube. In the older state of the art, the drain can only be advanced, not retracted.

German Gebrauchsmuster 86 14 013.2 discloses a design wherein the advancing tube communicates through a perforation with the ureter drain. This perforation allows advancing and retracting when the ureter drain is inserted by appropriate manipulation by means of the communication. Following proper emplacement of the ureter drain, the perforation must be removed. For that purpose the advancing tube and the mandrin are pulled in opposite directions, the mandrin resting against the distal tip of the ureter drain which may be closed. The pull is hard enough to tear the perforation.

A similar design is known from German Offenlegungsschrift 33 39 179 where the ureter drain also may be distally open. In this instance the endoscope, illustratively a suitable forceps, holds the ureter drain and the advancing hose then is pulled until the perforation tears.

However, such designs incur a series of drawbacks. It is difficult to manufacture the perforation such that it can withstand manipulation but will tear when desired. Because of inaccuracies of manufacture, it happens frequently that the perforation will not tear unless forces be applied which are great enough to entail danger of injury. Moreover, the irregularities of the perforation site may prove bothersome at the proximal end of the ureter drain at the bladder, and irritation may result when resting against the bladder wall. Moreover, the known devices require either a forceps to hold the ureter drain or a closed ureter drain end against which the mandrin rests. Limitations in design or construction result, which lead to problems The two above designs suffer from another restriction in practice in that while the ureter drain and the advancing tube are connected during manipulation, the mandrin on the other hand must be kept in its position to prevent it from slipping out. This is the reason that as a rule the proximal end of the advancing tube is clamped to the mandrin. The presence of this clamp necessitates additional manual operations when being applied or detached.

A ureter drain of the initially described kind is described in the published German Offenlegungsschrift 37 14 839 (published after the priority date of the present application). It does solve the problems of the cited earlier state of the art. The neck at the end of the advancing tube is inserted into the proximal end of the ureter drain and is clamped to the guide advanced by the advancing tube as far as into the ureter drain. Enough clamping force is generated thereby for the required manipulations of advancing and retraction to hold the advancing hose to the ureter drain. If now the ureter drain is properly emplaced in the body, then the end of the advancing tube projecting externally from the patient can be held in place and the guide retracted as far as over the clamping site. Thereby, the clamping is removed and the advancing tube can be pulled out.

Nevertheless this design incurs the drawback of difficult assembly when setting up the clamping. This work is carried out away from the patient, preferably at the factory, so that the ureter drain is furnished to the physician as a finished operable unit, where the guide is clamped to the advancing tube.

In the design shown in German Offenlegungsschrift 37 14 839, the neck of the advancing tube is in the shape of a sector of tube and is asymmetrically located to one side of the tube axis. In the presence of clamping, the mandrin itself rests with one side against the inside of the ureter drain and the other side against the neck. If during assembly the neck already has been inserted into the ureter drain and next the mandrin is advanced to achieve clamping, then the mandrin rubs on one side against the neck and on the other side against the ureter drain also and, upon further insertion into the ureter drain, attempts to move it forward by friction, that is away from the advancing tube. To prevent this from happening, the ureter drain must be kept stationary relative to the advancing tube using two hands, while the mandrin is advanced using a third hand. Accordingly, assembly by one person is quite difficult.

SUMMARY OF THE INVENTION

Therefore it is an object of the present invention to provide a ureter drain of the above described kind which, while retaining the advantages of the design cited initially, is easier to handle when being manipulated inside the patient and also when clamping or removing the connection.

Briefly described, the invention comprises a ureter drain catheter and positioning assembly comprising a flexible ureter drain catheter having an open proximal end and inner and outer substantially cylindrical surfaces, an advancing tube having an open distal end terminating in a cross sectionally reduced neck with an outer diameter smaller than the inner diameter of said drain catheter so that said distal end is insertable into the proximal end of said ureter drain catheter, and a mandrin insertable through said advancing tube and into said neck, said mandrin having an outer diameter greater than the inner diameter of said neck such that neck is clamped between said mandrin and said inner surface of said drain catheter and said mandrin is substantially centrally positioned in said catheter without making contact with said inner surface of said catheter.

In accordance with the invention, the neck is designed in such a way that it holds the mandrin at the clamping site on all sides without the mandrin making contact with the ureter drain tube. When the mandrin is advanced into the clamping site, this mandrin therefore only makes contact at that clamping site with the neck which it spreads until clamped against the ureter drain. The mandrin itself, however, does not make contact at that location with the ureter drain and therefore is not in high frictional engagement due to the clamping force against the ureter drain tube. When the mandrin is advanced into the clamping site, strong friction is applied only to the neck but not to the ureter drain tube. As the mandrin is advanced, the ureter drain tube remains seated on the neck without requiring that it be held in place there. Accordingly, assembly can be performed using two hands, one holding the advancing tube and the other shifting the mandrin. Assembly is thus simplified and made more economical.

It is also advantageous to form the neck so that it is in the form of a reduced diameter tube segment, compared with the remainder of the advancing tube, enclosing the mandrin from all sides and being expanded by this guide to clamp onto the ureter drain tube.

As an alternative, the neck advantageously is split longitudinally into tube sectors essentially symmetrical to the tube axis, illustratively two, three or four sectors being spread over the circumference. In this case, again, the mandrin only makes contact with the tube-sector strips of the neck without rubbing directly against the ureter drain tube at the clamping site.

BRIEF DESCRIPTION OF THE DRAWINGS

The invention is illustrated in schematic manner in the drawings, which form a part of this specification, and wherein:

FIGS. 1 through 3 are longitudinal axial sections at the clamping site with a tubular neck in different assembly stages;

FIGS. 4a through 4d are sections along line 4—4 of FIG. 3 showing four embodiments of the neck; and FIG. 5 is an axial sectional view of the neck of FIG. 4d.

DETAILED DESCRIPTION OF THE PREFERRED EMBODIMENT

FIGS. 1 through 3 and 4a show a first embodiment of the invention. A ureter drain tube or catheter 1, shown in axial section in FIGS. 1 through 3 and in cross-section in FIG. 4, is made of a soft plastic tube cut off to be open at the shown proximal end, that is the external end, and also is open at or near the distal end, not shown. The distal end opening (or openings) is commonly through the side of the tube near the end. The end itself is usually closed and rounded to facilitate pushing the tube through the ureter. An advancing tube 2, also shown in axial section in Figs. 1 through 3, is provided at its shown distal end with a neck 3, also in the form of a tube, with reduced inside and outside diameters relative to the advancing tube 2 as shown by FIGS. 1 through 3. The outside diameter of the neck 3 is reduced in such a manner that it is slightly less than the inside diameter of the catheter 1 within which it slides easily.

To assemble the advancing tube 2 to the catheter 1, the neck 3 is inserted axially in the direction of the arrow A shown in FIG. 1 into the drain 1, in other words, it moves from the separated position of FIG. 1 to the inserted position of FIG. 2. The advancing tube 2 with its neck 3 also consists of flexible tube material of a conventional type as regards such purposes.

Once the inserted position of FIG. 2 is achieved, a mandrin 4 is moved forward through the advancing tube in the direction of the arrow B. Mandrin 4 is flexible but of somewhat stiffer material, and is constructed, for example, as a wire coil or the like. Its tip is suitably rounded as shown.

The outside diameter of mandrin 4 must be smaller than the inside diameter of drain catheter 1 and larger than the inside diameter of neck 3. If the mandrin is then moved forward through the neck 3 until it extends into drain tube 1, that is, into the position shown in FIG. 3, then the flexible neck 3 widens in such a manner that it is firmly clamped between mandrin 4 and the inside surface of drain tube 1.

As shown in cross-section in FIG. 4a, mandrin 4 cannot touch drain tube 1 at the clamping site. At that site the mandrin makes frictional contact only with neck 3. If the mandrin 4 is moved ahead further, then friction occurs only with neck 3 and therefore frictional forces are imposed only on advancing tube 2.

To implement advancing, the proximal end of advancing tube 2 is held in place with one hand while the mandrin 4 is inserted with the other. The catheter 1 need not be held in place because during advancing the mandrin 4 will not transmit significant frictional forces to drain catheter 1. Elsewhere along drain catheter 1 the mandrin is significantly undersized, as compared with the inner diameter of the catheter, to allow slippage easily and without entailing significant friction.

This is also advantageous if during the operation mandrin 4 must be moved relative to the drain catheter 1, in particular if it must be retracted somewhat, which is a frequent occurrence. In that case no more need be done than seizing the end of the advancing tube 2 projecting from the patient and pulling the mandrin back somewhat relative to it. This can be done in a risk-free manner without thereby loosening the clamping relationship between advancing tube 2 and drain catheter 1.

The assembled system shown in FIG. 3 can be furnished in assembled form to the physician. He inserts this assembly into the patient, for instance through the urethra and the bladder, into the ureter as far as the kidney, wherein the drain 1 is positioned with its distal tip at the kidney and with its proximal tip at the bladder. The proximal end of advancing tube 2 stays outside the patient. Once the final position has been reached, mandrin 4 is withdrawn, releasing the clamping at neck 3 and the advancing tube 2 can be pulled out, the drain 1 remaining to provide a urine drain between kidney and bladder. Other medical applications also are conceivable.

In FIGS. 1 through 4a, the neck 3 is a closed tube, i.e., its wall is continuous around the periphery at the end thereof. However a slotted, strip-divided design of the neck also is feasible.

FIG. 4b shows a cross-section of a neck with two strips 5b. FIG. 4c shows an embodiment with three strips 5c and FIG. 5d shows an embodiment with four strips 5d.

In the embodiments of FIGS. 4b through 4d, the strips 5b, 5c and 5d essentially are symmetrical with respect to the tube axis and are circularly uniformly spaced in order to keep mandrin 4 separated on all sides from drain catheter 1, that is without rubbing against it at or near the clamping location.

The slitted embodiments of the neck shown in Figs. 4b through 4d may assume shapes at rest similar to the "necked-down" shape shown in FIG. 1, that is, with reduced outside diameters. However, as shown in FIG. 5 reflecting the embodiment of FIG. 4d, the neck portion also may have the same outside diameter as the advancing tube 2' while having a larger inside diameter. When being radially compressed, the strips 5d are made to assume a shape corresponding to that of the neck 3 of FIG. 1, such that the neck consisting of strips 5d is easily insertable into the drain 1.

What is claimed is:

1. A ureter drain catheter and positioning assembly comprising a flexible ureter drain catheter having an open proximal end and inner and outer substantially cylindrical surfaces;

an advancing tube having an open distal end terminating in a cross sectionally reduced neck with an outer diameter smaller than the inner diameter of said drain catheter so that said distal end is insertable into the proximal end of said ureter drain catheter, and a mandrin insertable through said advancing tube and into said neck, said mandrin having an outer diameter greater than the inner diameter of said neck such that neck is clamped between said mandrin and said inner surface of said drain catheter and said mandrin is substantially centrally positioned in said catheter without making contact with said inner surface of said catheter.

2. A ureter drain in accordance with claim 1, wherein said neck is a tubular portion of said advancing tube with inside and outside diameters less than those of said catheter.

3. A ureter drain according to claim 1 wherein said neck comprises a plurality of longitudinally separated strips having tubular sector shapes in crosssection, said strips being substantially symmetrical relative to the tube axis.

* * * * *